United States Patent [19]

Balbierz

[11] Patent Number: 5,759,179
[45] Date of Patent: Jun. 2, 1998

[54] NEEDLE AND VALVE ASSEMBLY FOR USE WITH A CATHETER

[75] Inventor: Daniel J. Balbierz, Redwood City, Calif.

[73] Assignee: Johnson & Johnson Medical, Inc., Arlington, Tex.

[21] Appl. No.: 777,897

[22] Filed: Dec. 31, 1996

[51] Int. Cl.$^6$ .................................................. A61M 5/32
[52] U.S. Cl. ........................... 604/272; 604/164; 604/248
[58] Field of Search .......................... 604/272, 164–167, 604/280, 247, 248, 249, 49, 51

[56] References Cited

U.S. PATENT DOCUMENTS

| | | | |
|---|---|---|---|
| 4,335,718 | 6/1982 | Calabrese | 604/272 |
| 4,535,773 | 8/1985 | Yoon | 604/51 |
| 4,874,377 | 10/1989 | Newgard et al. | 604/167 |
| 4,909,800 | 3/1990 | Gross | 604/272 |
| 4,917,668 | 4/1990 | Haindl | 604/167 |
| 4,966,586 | 10/1990 | Vaillancourt | 604/164 |
| 5,064,416 | 11/1991 | Newgard et al. | 604/167 |
| 5,066,288 | 11/1991 | Deniega et al. | 604/274 |
| 5,108,375 | 4/1992 | Harrison et al. | 604/167 |
| 5,215,526 | 6/1993 | Deniega et al. | 604/164 |
| 5,215,529 | 6/1993 | Fields et al. | 604/168 |
| 5,224,952 | 7/1993 | Deniega et al. | 606/184 |
| 5,256,149 | 10/1993 | Banik et al. | 604/164 |
| 5,267,965 | 12/1993 | Deniega | 604/164 |
| 5,338,311 | 8/1994 | Mahurkar | 604/195 |
| 5,352,205 | 10/1994 | Dales et al. | 604/158 |
| 5,387,197 | 2/1995 | Smith et al. | 604/164 |
| 5,399,167 | 3/1995 | Deniega | 604/164 |
| 5,419,766 | 5/1995 | Chang et al. | 604/110 |
| 5,514,100 | 5/1996 | Mahurkar | 604/195 |

*Primary Examiner*—John D. Yasko
*Attorney, Agent, or Firm*—Blakely, Sokoloff, Taylor & Zafman

[57] ABSTRACT

A needle assembly for use with a catheter. The needle assembly includes a valve disposed in a first shaft; the valve seals, when closed, fluid flow from a first side of the valve to a second side of the valve. The needle assembly further includes a needle system having a second shaft disposed parallel to the first shaft. The second shaft has a first dimension at a first position on the second shaft and has a second dimension at a second position on the second shaft. The second position corresponds to a position of the valve when the needle system is inserted into the valve such that the second position aligns with the position of the valve. In this manner, the valve is stressed less during storage when the needle system remains inserted through the valve. The valve is typically part of an introducer member which includes the first shaft and a flexible sheath which encloses a portion of the second shaft of the needle system.

22 Claims, 4 Drawing Sheets

NEEDLE AND VALVE ASSEMBLY FOR USE WITH A CATHETER

FIELD OF THE INVENTION

The present invention relates generally to the medical arts and more particularly to an improved needle and valve assembly.

BACKGROUND OF THE INVENTION

It is common practice in the medical field to insert flexible tubing into blood vessels for the infusion of various fluids and/or the monitoring of intravascular pressures. Moreover, it is common practice to use such flexible tubing for purposes of drainage from body tissues. One simple intravenous assembly of the prior art comprises a flexible introducer sheath having a rigid needle positioned axially within the sheath. The beveled tip of the hollow needle extends a short distance beyond the distal tip of the flexible sheath to permit easy penetration of the skin and underlying tissues. The needle tip is used to puncture a blood vessel, such as a vein. When the needle tip enters the target blood vessel, the blood immediately fills the lumen of the needle and advances proximally to a transparent receptacle on the needle hub where it may be viewed readily. The filling of the transparent receptacle allows the clinician to observe the so-called flashback of the blood which indicates the proper insertion of the needle into the blood vessel. Thereafter, the hollow needle is withdrawn, leaving the flexible sheath in place as a means for subsequent infusion of fluids through the sheath and/or as a means for connecting any catheter tubing which may be inserted through or connected with the sheath.

Upon withdrawal of the needle, a certain amount of blood invariably flows through the lumen of the sheath and flows out of the proximal end of the flexible sheath assembly. Consequently, regardless of how adept the user may be at attaching an appropriate solution administration line or other tubing to an introducer hub at the proximal end of the flexible sheath assembly, a certain amount of blood loss is likely to occur. While the amount of blood loss may not be a major concern, contamination from infected blood is often a concern. Moreover, air may also enter the patient's body and an air embolism may occur. Thus, it is desirable to stop the flow of blood out through the assembly of the flexible sheath.

The prior art often uses valves in a tube connected between the introducer hub and the flexible sheath. FIG. 1 shows an example of a prior art assembly which includes a needle 21 having a lumen 22 which is disposed axially within a flexible sheath 16. The flexible sheath 16 is coupled to an introducer assembly which includes an introducer hub 18 and a tube 12. The distal tip 21 of the needle 10 extends beyond the flexible sheath 22 when the assembly is fully assembled as shown in FIG. 1. The introducer hub 18 engages the needle hub 20 of the needle 10.

A valve having two valve elements 14a and 14b is shown as engaging the outer circumference of the needle 10 in order to seal off blood flow through the flexible sheath 16. There are numerous examples of valves in the prior art. For example, the valves described in U.S. Pat. No. 4,917,668 provide a seal within the tube 12 of the introducer assembly.

FIG. 2A shows a cross-sectional view of the assembly 9 through the line 2A of FIG. 1. As shown in FIG. 2A, the needle 10 includes the lumen 22 and is disposed axially within the tubing 12 of the introducer. The valve elements 14a and 14b tightly enclose the outer circumference of the needle 10 such that fluid flow is restricted from passing from one side of the valve to the other side of the valve. FIG. 2B shows an example of a prior art valve after the needle 10 has been removed. As shown in FIG. 2B, the valve elements 14a and 14b substantially close the inner lumen of the tubing 12 thereby preventing or substantially sealing the flow of fluids from one side of the valve to the other side of the valve through the tubing 12.

Such valves typically perform well enough if the needle and introducer sheath assembly is not stored with the needle inserted through the valve for a long period of time. After several months of storage, the assembly places considerable stress on the valve elements. This stress results in the valves not fully closing when the needle is removed upon use. This is shown in FIG. 2C wherein the valve elements 14a and 14b do not fully close after the needle has been withdrawn. With some valve materials, storage of the assembled needle and valve assembly for more than nine months will result in the accumulation of a significant amount of stress on the open valve, which causes the valve to close improperly and to leak. While the prior art has recognized this problem, the solutions in the prior art are often complicated valve structures which include springs to maintain the valve's functional properties. An example of such valve structures in shown in U.S. Pat. No. 4,917,668.

Thus it is desirable to provide an improved needle and valve assembly which is both simple and effective in reducing leakage through the valve even after many months of storage with the needle inserted through the valve.

SUMMARY OF THE INVENTION

The present invention provides a needle system and valve assembly for use, for example, with a catheter. The needle system and valve assembly includes a valve disposed in a first shaft of an introducer tube member. The valve attempts to seal, when closed, a fluid flow through an introducer tube member from one side of the valve to another side of the valve. The needle and valve assembly further includes a needle system having a second shaft disposed parallel to the first shaft. The second shaft is typically disposed axially within the flexible sheath of the introducer member as well as the first shaft of the introducer tube member. The second shaft has a first dimension at a first position on the second shaft, and has a second dimension at a second position. The second position corresponds to a position of the valve within the first shaft when the needle system is inserted into and properly positioned relative to the valve such that the second position on the needle system aligns with the position of the valve. This alignment normally occurs in storage when the needle remains inserted in the valve. Due to this geometry, the valve is opened less during storage, and thus the valve is stressed less during storage when the needle remains inserted in the valve. As a result, the valve, when required to be used after storage, will tend to close better after the needle is removed.

An embodiment of the present invention also includes a needle system having a first dimension at a first position and having a second dimension at a second position, wherein the second dimension of the needle system is for engaging a valve mechanism and is typically less than the first dimension.

In one embodiment of the present invention, the needle system may be hollow in one portion located generally in the first position and may be solid (not hollow) in the second position. Further, the hollow portion of the needle at the distal side of the valve may include an opening which is in addition to the opening of the hollow needle at the tip of the needle. This opening may provide for a small amount of flashback of blood or other fluid through the seal created by the valve while maximizing the reduction in stress on the valve. This embodiment may be useful in those cases where large volumes of flashback indication are not needed. Moreover, in embodiments where no flashback indication is required, the opening may be omitted.

DETAILED DESCRIPTION

The following describes various embodiments of the present invention, including the best presently contemplated mode of carrying out the present invention. This description is not to be taken in a limiting sense, but is made merely for the purpose of illustrating the general principles of the invention. The scope of the invention is best defined by the appended claims. Thus, various needle and valve configurations and geometries are illustrated herein for the purpose of describing the details of the present invention, and it will be appreciated that other alternative geometries and configurations may be utilized in accordance with the present invention. In other instances, well-known assemblies, devices, and processes are not described in detail in order to avoid unnecessarily obscuring the present invention.

Figure 3B:
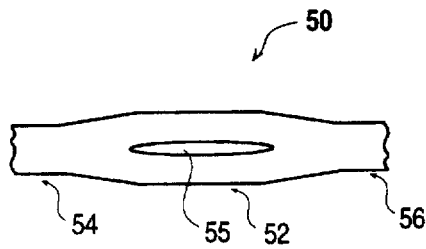
FIG. 3B shows another plain view of the needle system of FIG. 3A where the needle has been rotated 90° such that the plain view is taken from the position shown as 3B in FIG. 3A.
Figure 3A:
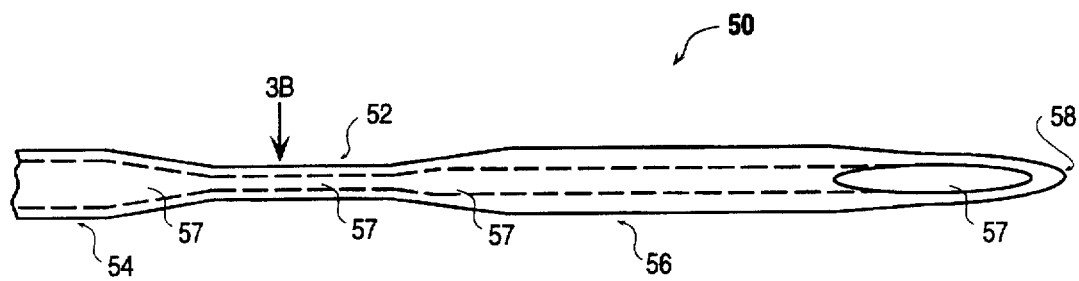
FIG. 3A shows a plain view of a needle system according to the present invention.

FIG. 3A shows a needle system according to an embodiment of the present invention. This needle 50 is generally a cylindrical object having a constricted portion which has been crimped in order to provide a reduced dimension relative to another dimension of another portion of the needle. The needle is crimped in the region where it passes through the valve so that the shelf life of the valve (and thus the assembly) is increased. The design reduces stress in the valve, which substantially eliminates valve failure and leakage. The crimping of the needle will not interfere with the functional properties of the needle, because the needle will still remain open to allow fluids to pass through the needle (and thus provide a flashback indication), and the needle will maintain its strength for puncturing into the desired insertion location.

The needle 50 shown in FIG. 3A includes a first tubular region 56 having a first dimension which is typically a first diameter and having a distal tip 58 which is used to puncture a blood vessel. The hollow lumen 57 conveys the blood from the distal tip 58 through the lumen 57 of the needle 50 to the proximal end of the needle which is adjacent to the tubular portion 54. The proximal end of the needle 50 typically includes a needle hub, and the tubular region 54 is typically coupled to the needle hub. A reduced region 52 of the needle 50 has a reduced dimension relative to the dimension of the tubular region 56. In the embodiment shown in FIG. 3A, a generally cylindrical needle having a constant diameter throughout its length is crimped in the region 52 in order to produce a region 52 which has a reduced dimension relative to a dimension of the tubular region 56 shown in FIG. 3A. The crimping operation, however, flattens the needle such that in another view which is 90° rotated relative to the view shown in FIG. 3A, the region 52 is enlarged relative to the tubular portions 56 and 54. This is shown in FIG. 3B which illustrates the needle 50 having the tubular regions 54 and 56 separated by the reduced region 52. The crimping mark 55 is shown in FIG. 3B, and it will be appreciated that this crimping mark is an artifact of the crimping process used to create the needle shown in FIGS. 3A and 3B.

Figure 1:
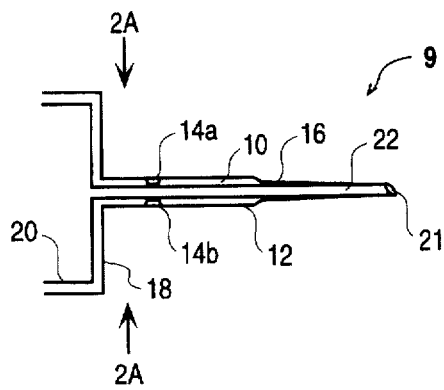
FIG. 1 shows a prior art needle and valve assembly within an introducer member.

It will be appreciated that the needle 50 will be typically attached to a needle hub 20 in the same fashion as in the prior art assembly 9 shown in FIG. 1. This needle hub may then be used as a position aligner in order to align the reduced region 52 relative to the valve 14a and 14b of the introducer member. This alignment in one embodiment aligns both the axial position of the reduced region 52 relative to the axial position of the valve within the introducer tube 12, as well as rotationally aligning the reduced region 52 relative to the valve such that the dimension of the reduced region 52 which exceeds the diameter of the tubular region 56 is aligned with the valve in a manner to reduce the stress of the valve. That is, this longer dimension of the reduced region 52 is aligned parallel with the sealing lips of the valve as shown in FIG. 4B.

Figure 4A:
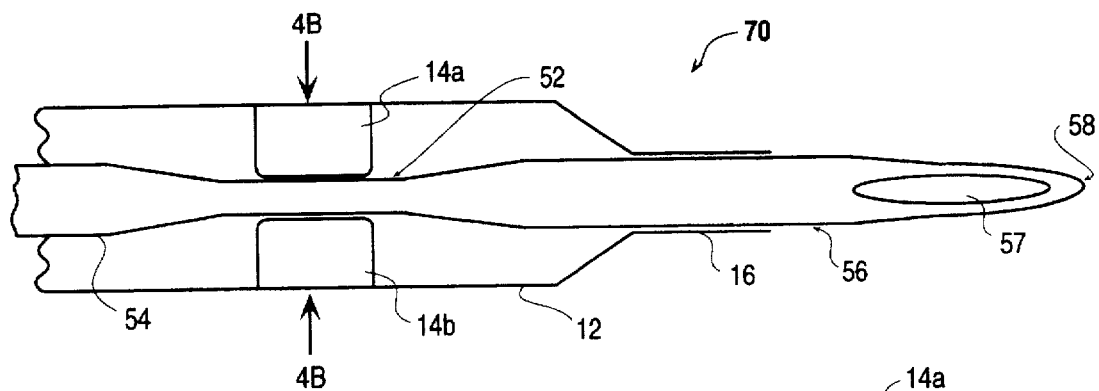
FIG. 4A shows a cross-sectional view of a needle system and valve assembly of the present invention.

FIG. 4A shows a cross-sectional view of the valve and needle assembly 70 of the present invention. In the embodiment shown in FIG. 4A, the needle 50 of FIG. 3A is used. The assembly 70 is shown in the storage position in which the needle 50 has been inserted into and through the valve formed by valve elements 14a and 14b. These valve elements 14a and 14b are similar to the valve elements 14a and 14b which are disposed in the cylindrical portion of the tube 12 of the introducer member. Thus, the needle of the present invention may be used with a valve introducer assembly of the prior art in order to produce the valve and needle assembly of the present invention. Also as shown in FIG. 4A, the introducer member includes a flexible sheath 16 which surrounds the proximal tubular portion 56 of the needle but does not cover the tip 58 or the lumen/opening 57 at the tip of the needle. The needle 50 is positioned both axially and rotationally relative to the valve elements 14a and 14b such that minimal stress is applied to the valve elements 14a and 14b. This is shown in both FIGS. 4A and 4B. The alignment of the reduced portion 52 both axially in the tube 12 of the introducer member and rotationally is achieved by two cooperating position aligners which form a mating engagement. This is shown in FIG. 1 as the needle hub 20 matingly engages a reciprocal introducer hub 18. This is further shown in FIG. 4C. FIG. 4C illustrates the mating engagement of the needle hub 20 into a reciprocal chamber in the introducer hub 18. Because the rectangular shape of the needle hub 20 can only fit within the introducer hub 18 in two ways (a first way and a second way which is rotated 180° relative to the first way), the rotational alignment of the reduced region 52 is achieved such that the reduced region 52 will only be placed within the valve in one of two orientations, either of which assures that the longer length of the reduced region 52 is disposed parallel with the sealing lips of the valve members 14a and 14b. This can also be seen in FIG. 4B. FIG. 4B shows that the reduced region 52 is aligned axially as shown in FIG. 4A as well as rotationally relative to the valve members 14a and 14b. That is, the long dimension of the reduced region 52 is substantially parallel to the sealing lips of the valve members 14a and 14b.

Other mechanisms for aligning the reduced portion relative to the valve will be appreciated by those of ordinary skill in the art upon reference to this disclosure. For example, the needle hub 20 may have a notch or key which fits into a slot or groove in the introducer hub 18, or the needle hub may have a shape which mates with a correspondingly mating shape on the introducer hub 18. Other configurations are feasible as long as the needle's reduced portion is properly aligned axially and rotationally relative to the valve.

Figure 2A:
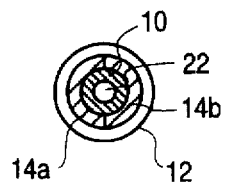
FIG. 2A shows a cross-sectional view of the prior art assembly of FIG. 1, with the cross-sectional view taken at line 2A as shown in FIG. 1.
Figure 2B:
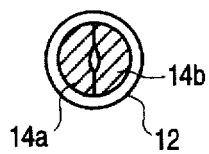
FIG. 2B shows another cross-sectional view of the prior art assembly after the needle has been removed, where the assembly has been stored for only a short period of time. This cross-sectional view of FIG. 2B is taken at line 2A as shown in FIG. 1 after the needle has been removed.
Figure 2C:
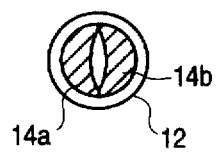
FIG. 2C shows a further cross-sectional view at line 2A of FIG. 1 after the needle has been removed following a long period of storage which has weakened the valve.
Figure 4B:
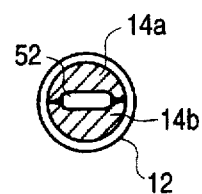
FIG. 4B shows another cross-sectional view of a needle system and valve assembly of the present invention taken at line 4B shown in FIG. 4A.
Figure 4C:
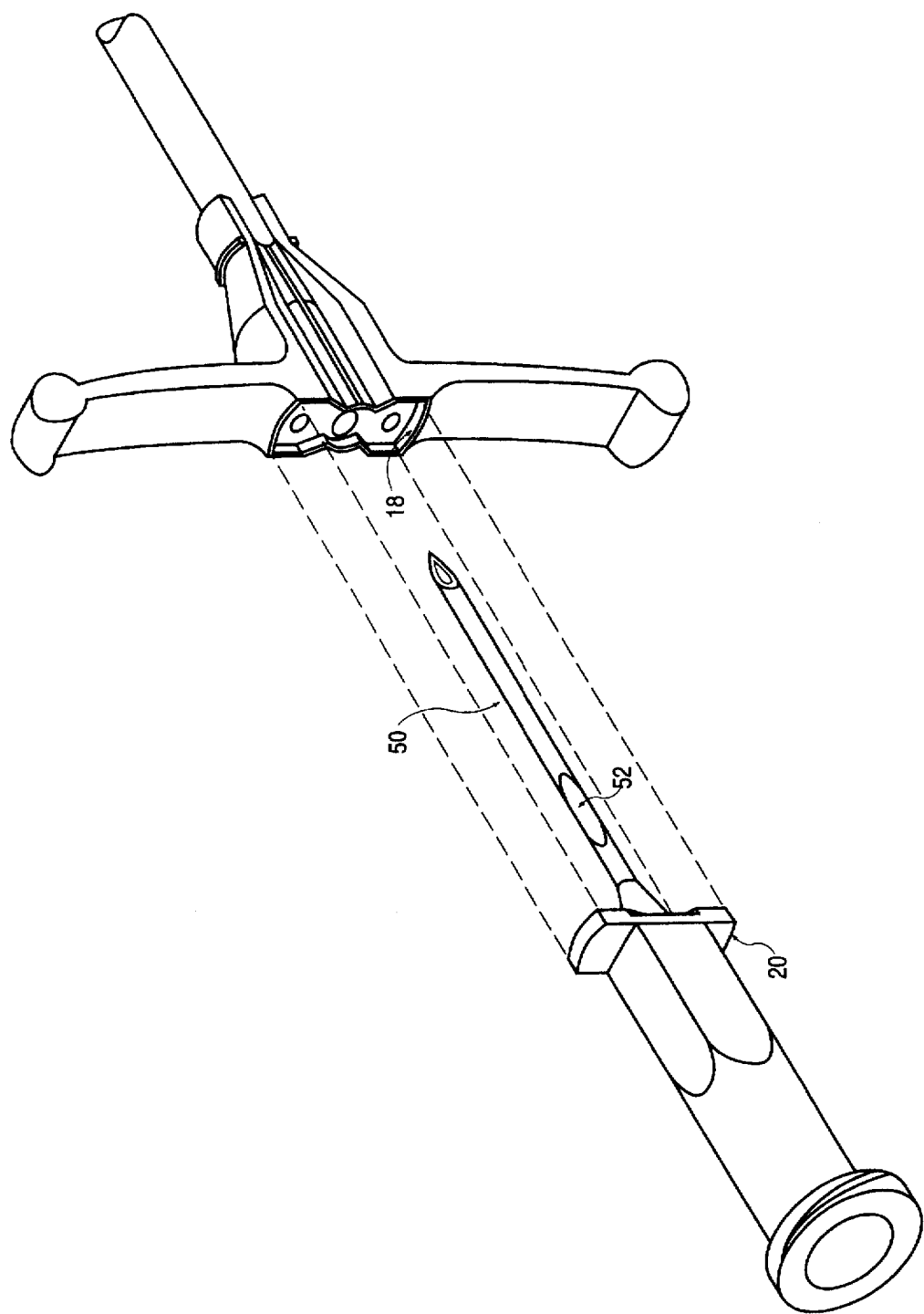
FIG. 4C shows the use of two positional aligners, one on each of the needle system and introducer members.

As shown in FIGS. 4A and 4B, the valve mechanism is forcefully pressing on the portion of the needle system disposed in the valve mechanism. This force is maintained during storage of the needle and valve assembly, and thus the valve mechanism is attempting to form a seal around the needle system. After the needle system is removed, the valve will close further, substantially sealing one side from the other side; an example of this substantial seal is shown in FIG. 2B. The invention provides an advantage relative to the prior art in that the needle and valve assembly may be packaged together (as shown in FIG. 4A) in sterile form and stored and be ready to use after retrieving the package from storage. This is unlike the prior art needle and valve assembly which works well enough only after short storage periods when fully assembled. It is preferable that the needle and valve be packaged in the fully assembled form (as shown in FIG. 4A) in order to avoid having to assemble the components immediately before use. Thus, a short IV catheter may use the needle and valve assembly of the invention and be packaged in sterile form and be ready to use immediately from storage even after months in storage. In this case, the valve will substantially stop leakage of blood through the short IV catheter.

Figure 5A:
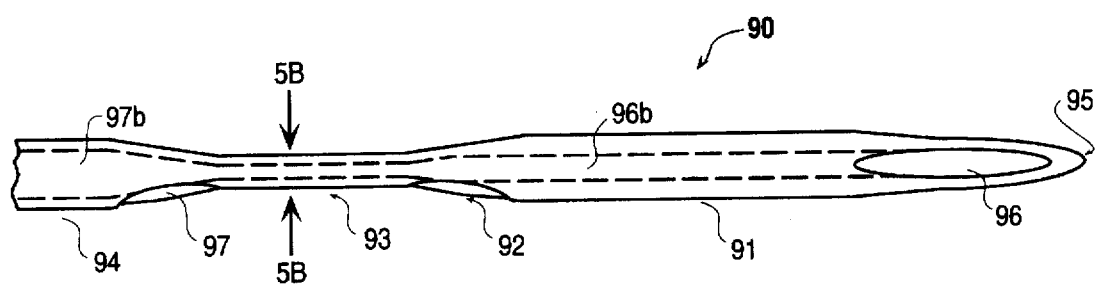
FIG. 5A shows a plain view of a needle system designed according to an alternative embodiment of the present invention.
Figure 5B:
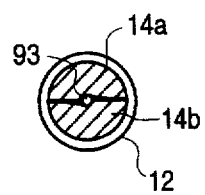
FIG. 5B shows a cross-sectional view of the needle according to an alternative embodiment of the present invention, where the cross-section is taken at line 5B as shown in FIG. 5A.

FIG. 5A shows an alternative embodiment of a needle system according to the present invention. In this embodiment, the reduced region 52 is replaced with a solid wire 93 which provides an even smaller cross-sectional area. This is shown in FIG. 5B which is a cross-sectional view of the needle system of FIG. 5A taken at line 5B. This cross-sectional view in FIG. 5B shows the needle system 90 of FIG. 5A in an introducer member and specifically at the cross-section through the valve members 14a and 14b in the tube 12 of the introducer member. As can be seen by comparing FIGS. 5B and 4B, the solid wire 93 occupies less space and thus places even less stress on the valve members 14a and 14b relative to the assembly shown in FIG. 4B. The needle system 90 shown in FIG. 5A includes three sections. The cylindrical hollow section 91 is at the distal end of the needle, and includes the needle's distal tip 95 and the opening 96 which is an entrance to the lumen 96b within the section 91. At the proximal end of the section 91 is another opening 92 which is adjacent to the reduced dimension region 93. A cylindrical region 94 is at the proximal end of the reduced region 93; this region 94 may or may not be hollow. In FIG. 5A, it is shown as hollow as it has an opening 97 and a lumen 97b. The embodiment shown in FIG. 5A attempts to provide the flashback feedback by providing blood to the opening 92 which may then be able to leak through the partially sealed valve which surrounds the reduced region 93 and then leak into the lumen 97b through opening 97.

Figure 6:
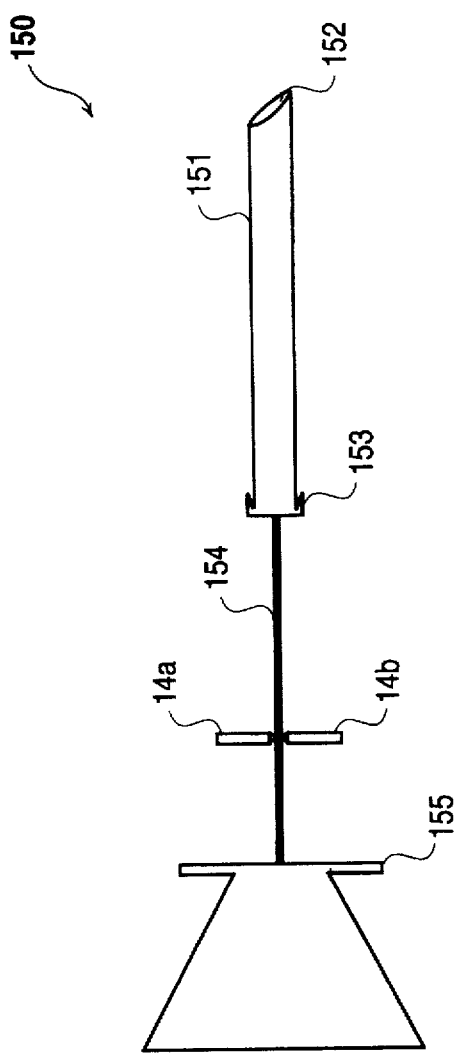
FIG. 6 shows a cross-sectional view of a needle system and valve assembly in another embodiment of the invention.

FIG. 6 shows another needle system and valve assembly according to the invention. The needle system 150 of FIG. 6 includes a distal hollow tubular portion 151 which includes a beveled distal tip 152. This tip 152 is used to puncture a vein. At the other end of the needle system 150 is a needle system hub 155. The distal hollow tubular portion 151 is coupled by a connector 153 to an extension 154 which extends from the needle system's hub 155. The extension 154 may be plastic and has a smaller cross-sectional area than the distal hollow tubular portion 151. The valve's members 14a and 14b align with the extension 154 of the needle system 150 during storage as shown in FIG. 6.

While the foregoing invention has been described with reference to various examples, the scope of the invention is indicated by the appended claims rather than the foregoing description. Numerous modifications and alternatives will be appreciated by those of ordinary skill in the art upon reference to the present description.

What is claimed is:

1. A needle assembly for use with a catheter, said needle assembly comprising:

a valve disposed in a first shaft, said valve for sealing fluid flow from a first side of said valve to a second side of said valve;

a needle system having a second shaft disposed parallel to said first shaft, said second shaft having a first dimension at a first position and having a second dimension at a second position corresponding to a third position of said valve in said first shaft.

2. A needle assembly as in claim 1 wherein said first dimension is larger than said second dimension.

3. A needle assembly as in claim 2 wherein said first dimension is a first diameter and said second dimension is a second diameter.

4. A needle assembly as in claim 2 wherein said second dimension is reduced relative to said first dimension by crimping said needle system at said second position, and wherein said needle system is hollow.

5. A needle assembly as in claim 4 wherein said needle system has a third dimension at said second position, said third dimension being larger than said first dimension.

6. A needle assembly as in claim 5 wherein said needle system further comprises a first position aligner which is for aligning said second position of said needle system relative to said valve and is for aligning said third dimension rotationally relative to said valve.

7. A needle assembly as in claim 6 further comprising a second position aligner coupled to said first shaft, said second position aligner for aligning with said first position aligner.

8. A needle assembly as in claim 2 wherein said needle system further comprises a position aligner which is for aligning said second position of said needle system relative to said valve.

9. A needle assembly as in claim 2 wherein said valve is part of a catheter introducer.

10. A needle assembly as in claim 2 wherein said second shaft comprises a first opening at a distal tip and a second opening near said second position and a third opening near said second position.

11. A needle assembly as in claim 1 wherein said second position comprises a solid section of said needle system.

12. A needle assembly comprising:

a valve disposed in a first shaft, said valve for sealing fluid flow from a first side of said valve to a second side of said valve;

a needle system having a second shaft disposed parallel to said first shaft, said second shaft having a first dimension at a first position and having a second dimension at a second position corresponding to a third position of said valve in said first shaft.

13. A needle assembly as in claim 12 wherein said first dimension is larger than said second dimension.

14. A needle assembly as in claim 13 wherein said first dimension is a first diameter and said second dimension is a second diameter.

15. A needle assembly as in claim 13 wherein said second dimension is reduced relative to said first dimension by crimping said needle system at said second position, and wherein said needle system is hollow.

16. A needle assembly as in claim 15 wherein said needle system has a third dimension at said second position, said third dimension being larger than said first dimension.

17. A needle assembly as in claim 16 wherein said needle system further comprises a first position aligner which is for aligning said second position of said needle system relative to said valve and is for aligning said third dimension rotationally relative to said valve.

18. A needle assembly as in claim 17 further comprising a second position aligner coupled to said first shaft, said second position aligner for aligning with said first position aligner.

19. A needle assembly as in claim 13 wherein said needle system further comprises a position aligner which is for aligning said second position of said needle system relative to said valve.

20. A needle assembly as in claim 13 wherein said valve is part of a catheter introducer.

21. A needle assembly as in claim 13 wherein said second shaft comprises a first opening at a distal tip and a second opening near said second position and a third opening near said second position.

22. A needle assembly as in claim 12 wherein said second position comprises a solid section of said needle system.

* * * * *